(12) United States Patent  
Cooper

(10) Patent No.: US 9,744,497 B2  
(45) Date of Patent: Aug. 29, 2017

(54) CONTINUOUS DIFFUSION DENUDING WITH MOVING DENUDING SURFACE

(71) Applicant: Cooper Environmental Services LLC, Beaverton, OR (US)

(72) Inventor: John Arthur Cooper, Beaverton, OR (US)

(73) Assignee: Cooper Environmental Services LLC, Beaverton, OR (US)

(*) Notice: Subject to any disclaimer, the term of this patent is extended or adjusted under 35 U.S.C. 154(b) by 128 days.

(21) Appl. No.: 14/919,462

(22) Filed: Oct. 21, 2015

(65) Prior Publication Data

US 2016/0045863 A1 Feb. 18, 2016

Related U.S. Application Data

(62) Division of application No. 13/531,457, filed on Jun. 22, 2012, now Pat. No. 9,199,192.

(51) Int. Cl.
| | |
|---|---|
| *B01D 47/00* | (2006.01) |
| *B01D 53/83* | (2006.01) |
| *B01D 53/64* | (2006.01) |
| *B01D 53/68* | (2006.01) |
| *G01N 1/40* | (2006.01) |
| *B01D 53/96* | (2006.01) |

(52) U.S. Cl.
CPC ............ *B01D 53/83* (2013.01); *B01D 53/64* (2013.01); *B01D 53/68* (2013.01); *B01D 53/96* (2013.01); *G01N 1/405* (2013.01); *G01N 1/4044* (2013.01); *B01D 2251/108* (2013.01); *B01D 2257/2045* (2013.01)

(58) Field of Classification Search
None
See application file for complete search history.

(56) References Cited

U.S. PATENT DOCUMENTS

| H188 H | * | 1/1987 | Thomson | ............ G01N 15/0618 |
| | | | | 378/45 |
| 6,872,370 B2 | * | 3/2005 | Cooper | .................. B01D 53/64 |
| | | | | 423/210 |

* cited by examiner

*Primary Examiner* — Anita Nassiri Motlagh
(74) *Attorney, Agent, or Firm* — Jared S. Goff; Goff Patent Law PLLC

(57) ABSTRACT

A duct can be configured to receive a denuding gas flow. A solid denuding surface that is connected to a drive system can be configured to move the solid denuding surface within the duct while the solid denuding surface is continuously concentrating one or more gas-phase species from the denuding gas flow on the denuding surface. Also, a denuding gas flow can be passed along a denuding surface to concentrate one or more gas phase species from the denuding gas flow onto the denuding surface with a diffusion denuding action. The denuding surface can be moved while continuing to concentrate the one or more gas phase species from the denuding gas flow onto the denuding surface.

20 Claims, 4 Drawing Sheets

CONTINUOUS DIFFUSION DENUDING WITH MOVING DENUDING SURFACE

RELATED APPLICATIONS

The present application is a divisional of U.S. application Ser. No. 13/531,457, filed Jun. 22, 2012, which is incorporated herein by reference. If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

BACKGROUND

A process by which one or more specific reactive gas phase species (i.e., a pure gas phase species, a vapor phase species, and/or a species that is a combination of gas and vapor phases) are extracted from a gas flow (which may be a pure gas flow or an aerosol that includes suspended particles and/or droplets) by bringing the molecules of the gas phase species into contact with a reactive denuding surface through diffusion is referred to as diffusion denuding of the gas flow. Diffusion denuding can take place either passively (without moving the gas flow across the denuding surface) or actively (by moving the gas flow across the denuding surface).

SUMMARY

The description herein relates to a moving reactive surface across which is passed a moving gas flow that is continuously being denuded of specific reactive gas phase species contained therein (i.e., that continues to be denuded even while the surface moves). Continuously moving a gas flow across a moving solid reactive surface (the denuding surface) can facilitate continuous concentration and collection of targeted gas phase reactive species onto the solid denuding surface and may allow subsequent analysis by one or more of a variety of methods. In addition, denuding of these reactive gas phase species from the gas flow can be used to control and prevent the emission of these gas phase species.

According to one embodiment, a duct is configured to receive a denuding gas flow. A solid denuding surface can be connected to a drive system, which can be configured to move the solid denuding surface within the duct while the solid denuding surface is continuously concentrating one or more gas-phase species from the denuding gas flow on the denuding surface.

According to another embodiment, a denuding gas flow can be passed along a denuding surface to concentrate one or more gas phase species from the denuding gas flow onto the denuding surface with a diffusion denuding action. The denuding surface can be moved while continuing to concentrate the one or more gas phase species from the denuding gas flow onto the denuding surface.

This Summary is provided to introduce a selection of concepts in a simplified form. The concepts are further described below in the Detailed Description. This Summary is not intended to identify key features or essential features of the claimed subject matter, nor is it intended to be used to limit the scope of the claimed subject matter. Similarly, the invention is not limited to implementations that address the particular techniques, tools, environments, disadvantages, or advantages discussed in the Background, the Detailed Description, or the attached drawings.

BRIEF DESCRIPTION OF THE DRAWINGS

The description and drawings may refer to the same or similar features in different drawings with the same reference numbers.

DETAILED DESCRIPTION

This description relates to a moving denuding surface that chemically reacts with specific reactive gas phase species such as hydrogen chloride (HCl), chlorine (Cl2), sulfur trioxide (SO3), hydrogen sulfide (H2S), etc. in a gas flow that is moving across this reactive surface. Such diffusion denuding can be applicable to pre-concentration of these and other gas phase species onto a solid surface prior to analysis with a variety of elemental and chemical sensors such as X-ray fluorescence, laser induced ablation spectroscopy, colorimetry, etc. The description below will describe one or more methods of extracting and possibly analyzing these gas phase species, and one or more apparatuses used to perform the extraction and possibly the subsequent analysis. Although the described techniques and tools can be used for analysis of species in a gas flow, they can also be applied in the emission control field where a continuously refreshed surface can be moving through an emission aerosol extracting reactive gas phase species.

This arrangement can produce benefits that are not present in or predictable from prior analysis and removal techniques and tools. For example, the tools and techniques described herein may reduce adverse effects such as fouling of the denuding surface by particulate matter (PM) dust and/or exceeding the denuding surface's reactive capacity. However, the subject matter defined in the appended claims is not necessarily limited to the benefits described herein. A particular implementation of the invention may provide all, some, or none of the benefits described herein. Although operations for the various techniques are described herein in a particular, sequential order for the sake of presentation, it should be understood that this manner of description encompasses rearrangements in the order of operations, unless a particular ordering is required. For example, operations described sequentially may in some cases be rearranged or performed concurrently. Techniques described herein with reference to flowcharts may be used with one or more of the systems described herein and/or with one or more other systems. Moreover, for the sake of simplicity, flowcharts may not show the various ways in which particular techniques can be used in conjunction with other techniques.

I. Analytical Apparatus

A. Example of the Apparatus

Figure 1:
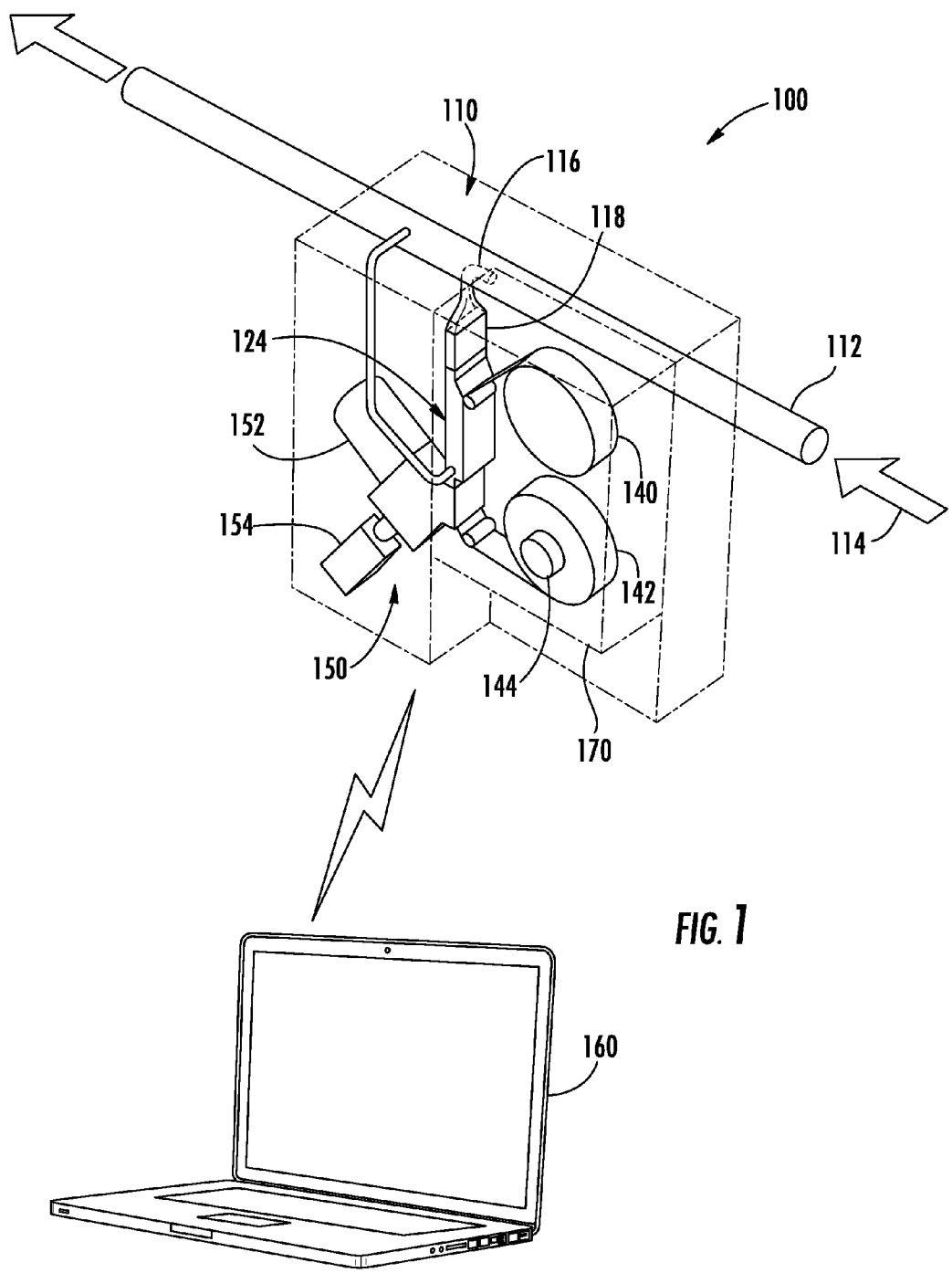
FIG. 1 is a schematic illustration of an analytical apparatus configured to perform continuous diffusing denuding with a moving denuding surface.

Referring to FIG. 1, an example of an analytical apparatus (100) is illustrated in schematic form. The apparatus can include a flow control system (110) that can provide a gas flow to be analyzed. For example, the flow control system (110) can include a slip stream flow duct (112), which can transport a portion (the slip stream flow (114)) of a flow, such as a portion of a stack gas flow from a stack to a sample inlet (116). For example, the slip stream flow duct (112) may begin at a probe located within a stack wherein stack gas is flowing. The sample inlet (116) may be a probe located within the slip stream flow (114) in the slip stream flow duct (112).

Figure 2:
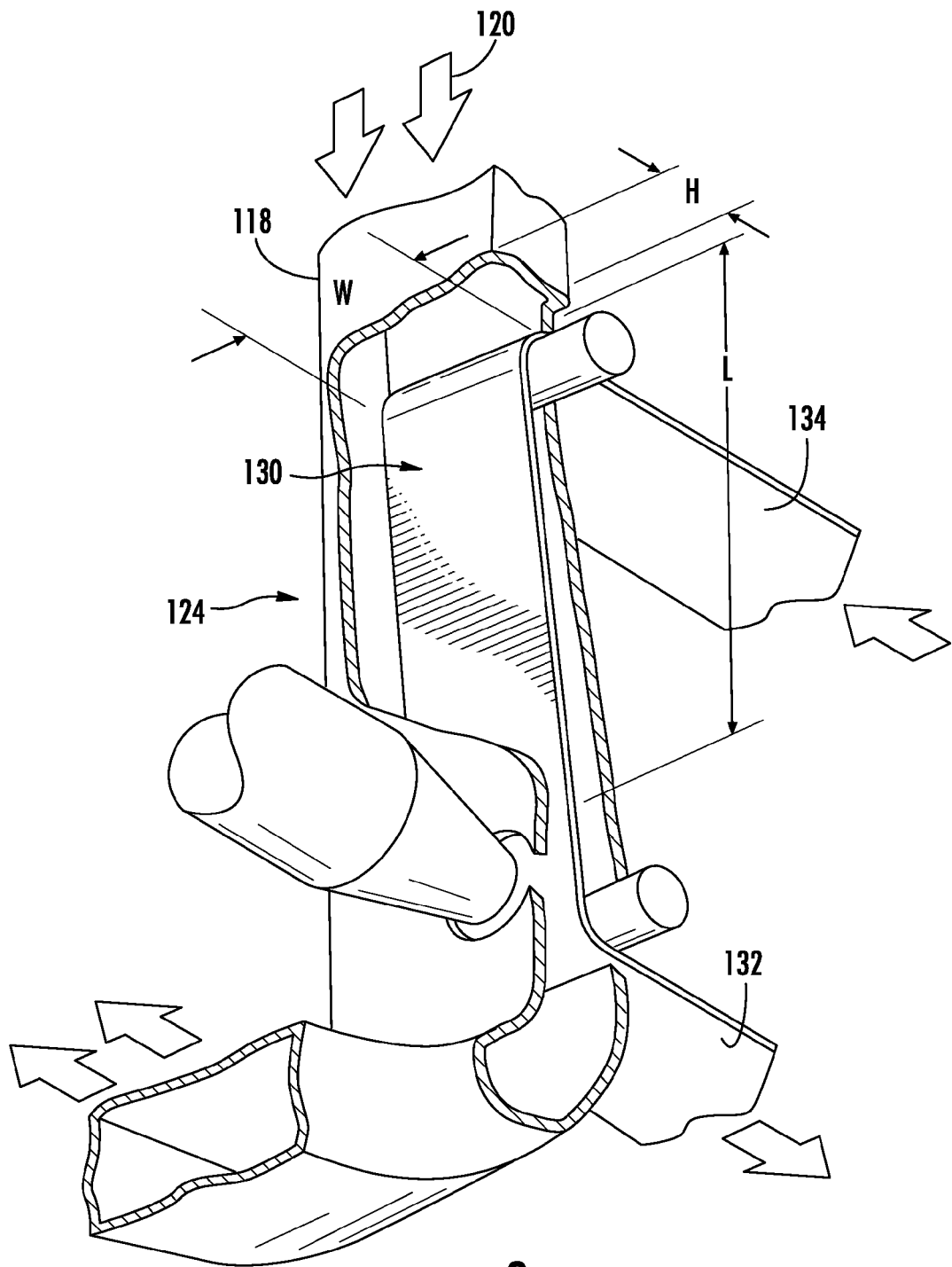
FIG. 2 is a broken away sectional view of an exposure zone of an analytical apparatus such as the apparatus of FIG. 1.

Referring now to FIGS. 1-2, the sample inlet (116) can lead to a sample duct (118) that carries a sample flow (120) from the sample inlet (116) and through an exposure zone (124), where the sample flow (120) can flow along a denuding surface (130). For example, the denuding surface (130) can be a surface of a coating (132) on a substrate such as a tape (134).

The coating (132) can include reactive materials that can react with and trap one or more gas phase species from the sample flow (120) on the denuding surface (130) when the molecules of the species contact the denuding surface (130). The type of the coating (132) can be selected based on its ability to trap the one or more species of interest while excluding other, potentially interfering species. While it can be beneficial for the coating (132) to be selective in the species that it traps, such selective properties need not be perfect. Some sensors, such as X-ray fluorescence may provide additional selectivity as well as analyte quantification. As an example, the coating (132) may include elemental iodine if a species to be denuded is mercury. As another example, Orthotolidine could be used. Also, the same types of coatings that have been used in batch denuding applications could be used (e.g., sodium bicarbonate, sodium hydroxide, some Glycerin could be added, etc.).

The denuding surface (130) could be the surface of a tape or some other type of solid substrate. For example, the substrate could be a string, etc. The substrate could be made of one or more of various different types of materials, such as Teflon, Mylar, Polycarbonate, biomembrane filter tape such as a coated polyethersulfone filter tape (where the aerosol can be directed across the filter tape instead of through the filter tape).

As an example, Orthotolidine can be dissolved in acetone, and the substrate can be dipped in the resulting solution to form the coating (132). As another example, elemental iodine can be dissolved in Pentane, and the substrate can be dipped in the resulting solution to form the coating (132).

The tape (134) can be fed from a tape dispensing spool (140), into and along the exposure zone (124) in the sample duct (118), out of the exposure zone (124), and onto a tape take-up spool (142). A drive system can include a controlled-rate motor (144) such as a step motor, which can feed the tape (134) from the tape dispensing spool (140) to the tape take-up spool (142). The sample duct (118) can lead from the exposure zone back to the slip stream flow duct (112), so that the sample flow (120) can flow back to the slip stream flow (114) after diffusion denuding of one or more species on the denuding surface (130) has occurred.

The apparatus (100) can also include a sensor (150), which can be a chemical sensor that utilizes one or more sensing techniques such as X-ray fluorescence, laser induced ablation spectroscopy, colorimetry, etc. In the illustrated example in FIG. 1, the sensor (150) is an X-ray fluorescence sensor with an X-ray tube (152) and an X-ray detector (154). The sensor (150) can transmit its sensing results to a data processing and reporting system (160). For example, the data processing and reporting system (160) can include a programmable logic controller, a computer running software, and/or other processing and reporting systems. The data processing and reporting system (160) may also include one or more processors, memory, input devices, output devices, buses, connections between such devices, etc. For example, the data processing and reporting system (160) may include a keyboard, mouse, trackball, touch screen, etc. for receiving user input. The data processing and reporting system (160) may also include a computer display for displaying results of the data processing, for prompting for user input, etc. The data processing and reporting system (160) can include instructions (e.g., code and/or logic circuits) that when executed can process data from the sensor (150) and report results of the processing in a manner that allows the sensor (150) to continue collecting data while the processing occurs. For example, the sensor (150) may store and periodically send data to the data processing and reporting system (160). While the data processing and reporting system (160) is processing and/or reporting such data, the sensor (150) may continue sensing and collecting data to be sent to the data processing and reporting system (160) in a later transmission. Thus, the sensor (150) may continuously sense the presence of one or more denuded species while the denuding surface (130) is moving, allowing the denuding to be performed continuously as well.

The apparatus (100) can also include a housing (170), which can house the sample duct (118), the denuding surface (130) in the exposure zone (124), the tape dispensing spool (140), the tape take-up spool (142), and the sensor (150). The housing (170) can be sealed (though it may not be entirely leak-proof) to decrease leakage along the flow path for the denuding surface (130) and the sample flow (120). Additionally, pressurized air may be introduced into the housing to help keep the sample flow (120) contained to its flow path, such as in the exposure zone (124).

The housing (170) could contain different components. For example, the sensor (150) could be located at least partially outside the sealed housing (170). As another example, at least a portion of the data processing and reporting system (160) could be contained in the housing (170). Also, a distinction between the sensor (150) and the data processing and reporting system (160) could be blurred. For example, the sensor (150) can include some processing capability.

B. Quantitative Diffusion Denuding Analysis Examples

Figure 3:
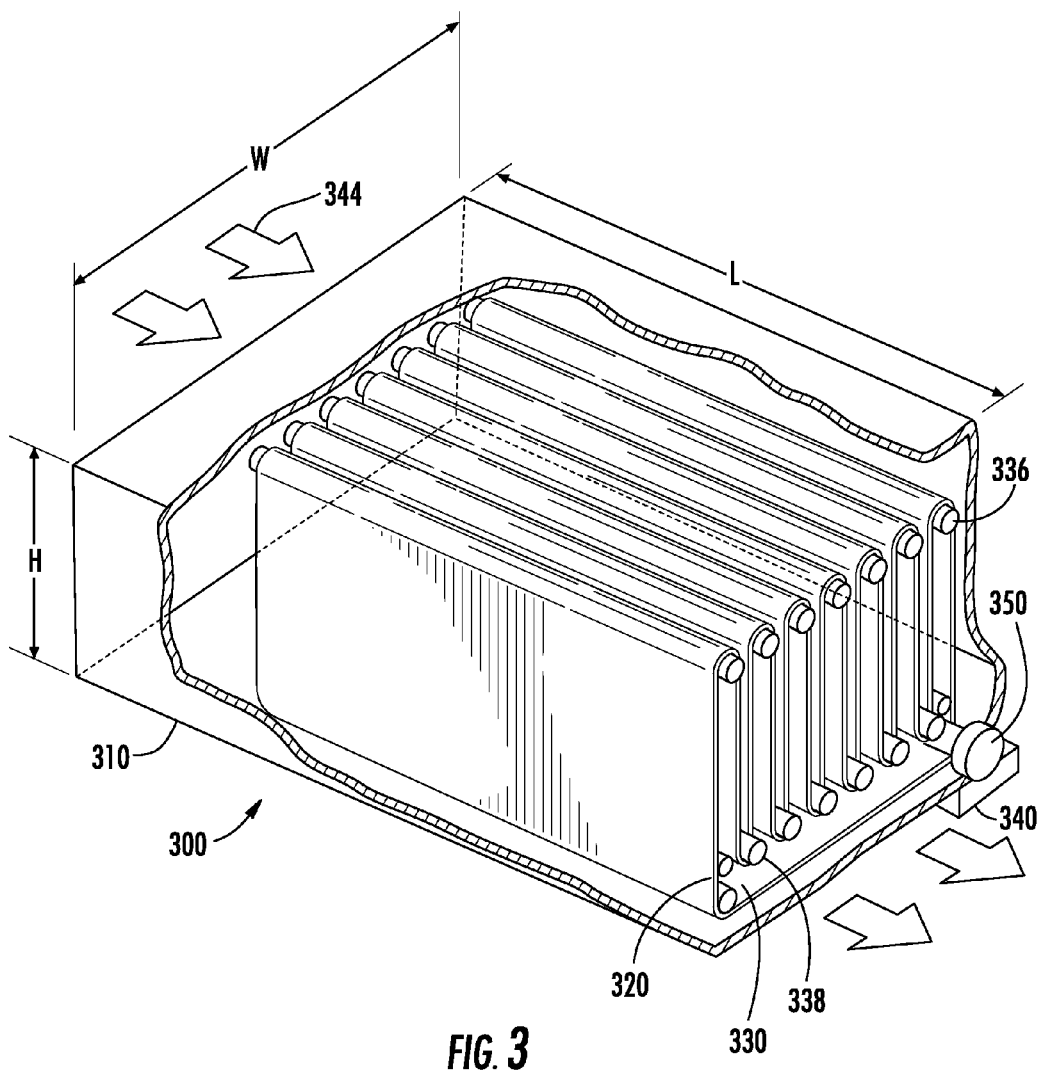
FIG. 3 is a broken away sectional view of a continuous diffusion denuding apparatus for controlling emissions.
Figure 4:
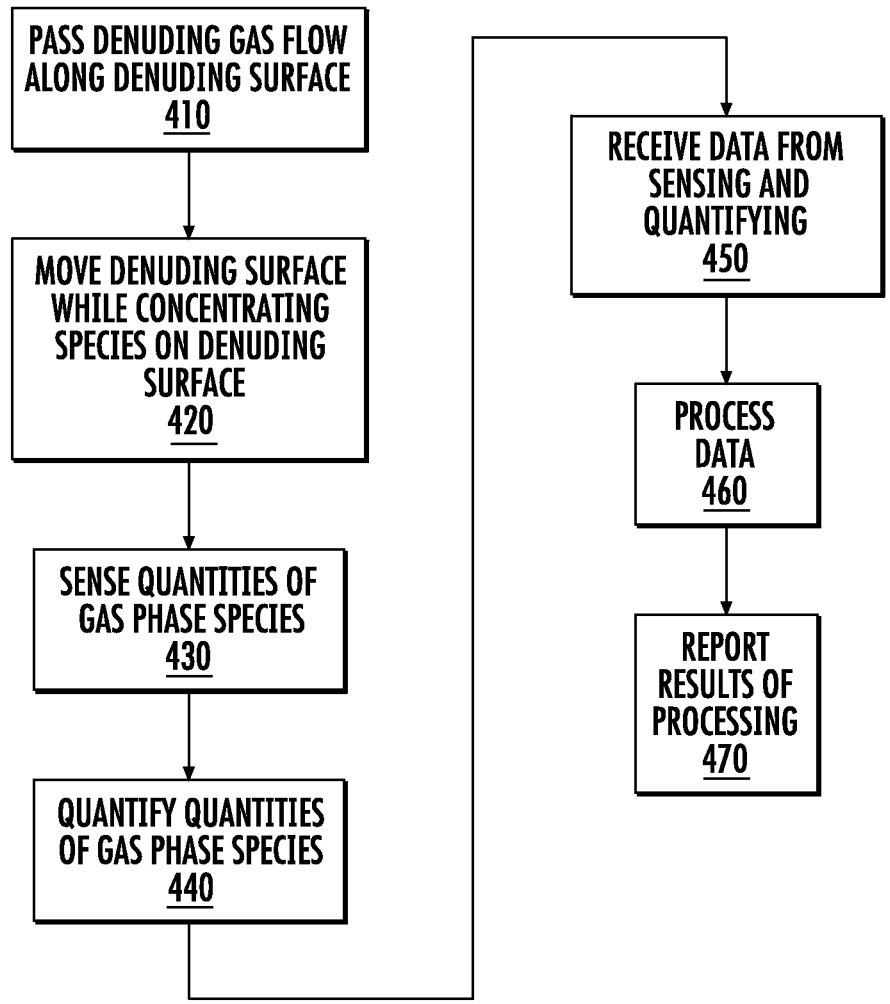
FIG. 4 is a flowchart of a technique for continuous diffusion denuding with a moving denuding surface.

A schematic illustration of the exposure zone is shown in FIG. 2, which identifies parameters (W, H, and L) that can affect the effectiveness of denuding in the apparatus (100). Similar parameters are illustrated in FIG. 3, which will be discussed more below. As noted above, the sample flow is directed through the sample duct (118) and along the moving denuding surface (130), which is moving at a rate R. As illustrated, the denuding surface (130) can be oriented vertically. Accordingly, the particles can pass through the exposure zone without depositing significant amounts of the particles on the moving denuding surface (130) while the gas molecules, which can move at much higher velocities than particles, can react with the denuding surface (130) to form a solid deposit on the denuding surface (130). With enough time, almost all of the target gas phase species molecules will contact and be trapped on the denuding surface (130), thereby being removed from the sample flow (120). By adjusting the flow rate of the sample flow (120), the residence time during which the gas is in contact with the denuding surface (130) can be adjusted to assure adequate residence time for a high removal efficiency.

As is illustrated in FIG. 2, a parameter W is the width of the exposed area of the denuding surface (130) and of the sample duct (118) in the exposure zone (124). A parameter H is the height of the sample duct (118) in the exposure zone (124), measured normal to the denuding surface (130) in this example. A parameter L is the length of the denuding surface (130) exposed to the sample flow (120).

The following table illustrates some parameters, along with some example ranges, and a specific example value for each parameter. The parameters will also be discussed below, following the table. It should be understood that the invention is not limited to these example values or ranges unless so stated in the claims.

| Parameter Symbol & Description | Example Range | Example Value |
|---|---|---|
| $A_f$ = Gas flow, cross sectional area (H × W) | <0.1 cm to 10 cm | 0.1 cm × 2 cm = 0.2 cm$^2$ |
| $A_t$ = Exposed tape area (L × W) | 1 to 100 cm$^2$ | 2 cm × 5 cm = 10 cm$^2$ |
| C = Concentration of analyte in gas | PPTV (parts per trillion by volume) to PPMV (parts per million by volume) | 1 to 30 PPMV |
| D = Aerial density of analyte on tape | ng/cm$^2$ to mg/cm$^2$ | 10 μg/cm$^2$ |
| $D_l$ = Aerial density detection limit | 0.01 to 10 ng/cm$^2$ | 1 ng/cm$^2$ |
| $D_m$ = Maximum aerial density (capacity) | 1-100 μg/cm$^2$ | 20 μg/cm$^2$ |
| F = Sampling flow of stack gas | 0.01-10 lpm | 0.1 lpm |
| H = Height of opening for gas flow | 0.01-1 cm | 0.1 cm |
| L = Length of tape exposed to gas | 1-30 cm | 5 cm |
| R = Rate of tape use | 0.001-0.01 cm/sec | 0.008 cm/sec |
| $T_e$ = Gas exposure time | 0.001-0.1 sec | >0.1 sec (target) |
| $T_t$ = Tape travel time (L/R) | 100-1000 sec | 500 sec |
| $V_e$ = Velocity of gas (F/Af) | 1-1,000 cm/sec | 10 cm/sec |
| $V_o$ = Volume of gas denuded | 0.01-1,000 liters | 1 liter |
| W = Width of exposed area of tape | .02-20 cm | 2 cm |

Following are some examples of parameters for analyzing HCl in emissions from Portland cement plants, coal-fired power plants, incinerators, and industrial boilers. In these examples, the "Limit" is an example of a regulatory limit for concentration of HCl in emissions, "Capacity" is the HCl concentration capacity that could be sampled by the reactive denuding surface, "Design Concentration" is the HCl concentration for which the apparatus is designed, and limits of detection ("LOD") are the lower HCl concentration limits that can be detected with the apparatus.

1. Portland Cement Plant and Coal Fired Power Plant
   a. Limit ~3 PPMV (5 mg/m$^3$)
   b. Capacity ≥20 mg/m$^3$
   c. Design Conc. ~1 PPMV (~2 mg/m$^3$)
   d. LOD ≤0.1 PPMV
2. Incinerators & Industrial Boilers
   a. Limits ~30 PPMV (50 mg/m$^3$)
   b. Capacity ≥200 mg/m$^3$
   c. Design Conc. ~10 PPMV (~20 mg/m$^3$)
   d. LOD ≤1 PPMV
3. Examples for New Regulations
   a. Limits ≤0.1 PPMV (~0.2 mg/m$^3$)
   b. Capacity ≥0.8 mg/m$^3$
   c. Design Con. ~0.05 PPMV (~0.08 mg/m$^3$)
   d. LOD ≤0.01 PPM With these parameters in mind, along with the following specific example target design parameters, the equation relating the aerosol concentration of the species to the measured concentration of the species on the moving denuding surface (130) can be derived as indicated below. Target design parameters: W=2 cm; L=5 cm; $A_t$=10 cm$^2$; H=0.1 cm; $A_f$=0.2 cm$^2$; R=0.008 cm/sec; F=0.1 lpm; $V_e$=8.3 cm/sec.

The exposure time ($T_e$) available to denude the gas sample can be calculated according to the following equation.

$$T_e = \frac{L}{V_e} = \frac{5 \text{ cm}}{8.3 \text{ cm/sec}} = 0.60 \text{ sec } @0.1 \text{ lpm}$$

The time for the tape to move the 5 cm of exposure length ($T_t$=tape travel time) can be calculated according to the following equation.

$$T_t = \frac{L}{R} = \frac{5 \text{ cm}}{0.008 \text{ cm/sec}} = 625 \text{ sec}$$

The volume of gas ($V_o$) exposed to the tape in 625 seconds can be calculated according to the following equation.

$$V_o = FT_t = (100 \text{ cc/min})(10.4 \text{ min}) = 1,040 \text{ cm}^3$$

The analyte aerial density (the density D of the species on the denuding surface) can be calculated according to the following equation:

$$D = \frac{V_0 C}{A_t} = [(1.038 \text{ l})(1 \text{ mg/m}^3)]/10 \text{ cm}^2 = 100 \text{ ng/cm}^2$$

$$D = (FL/RA_t)C < D_m \sim 20 \text{ μg/cm}^2$$

The following equation can be obtained by solving the above equation for the analyte gas concentration (C).

$$C = \frac{RA_t}{FL}D = \left[\left(\frac{R}{A}\right)\left(\frac{A_t}{L}\right)\right]D = KD$$

In this equation, $$\left(\frac{R}{F}\right)$$

is a controlled constant that can be controlled by controlling the flow rate of the sample flow (120) and the rate of the moving denuding surface (130). The term $$\left(\frac{A_t}{L}\right)$$

is a design constant that depends on the geometry of the apparatus (100). These two terms $$\left(\left(\frac{R}{F}\right) \text{ and } \left(\frac{A_t}{L}\right)\right)$$

can be multiplied together to form a constant K, which can be used to convert the density D to the concentration C of the species in the aerosol. This equation assumes 100% denuding efficiency. If the denuding efficiency is less than 100% by a significant value, a factor can be introduced into the conversion equation above to correct for such an inefficiency.

While an example apparatus (100) and example calculations for such an apparatus have been discussed above, changes may be made within the scope of the disclosure herein. For example, different configurations, materials, etc. may be used for the apparatus and for techniques for using the apparatus.

II. Continuous Diffusion Denuding Apparatus for Controlling Emissions

Referring now to FIG. 3, an example of continuous diffusion denuding for controlling emissions will be discussed. FIG. 3 illustrates an example of an emission control apparatus (300). The apparatus (300) can include a flow duct (310) surrounding a series of denuding surfaces (320) formed by a flexible sheet (330) wound over and under a series of top rollers (336) and bottom rollers (338) to form a serpentine pattern. The denuding surfaces (320) can be positioned parallel to the direction of movement of a gas flow (344) that includes one or more species to be controlled. A drive system (350) can engage the flexible sheet (330) to move the sheet while one or more gas phase species are being concentrated on the denuding surfaces (320) of the flexible sheet (330). For example, the drive system (350) can include a drive motor.

The apparatus (300) can also include a treatment zone (340), which can refresh the reactive properties of the denuding surfaces (320) as they pass through the treatment zone. For example, the treatment zone (340) could subject the surfaces (320) to chemical solutions, heat, radiation, etc. The refreshing of the surfaces (320) could include regenerating surface activity and/or recovering and controlling the one or more gas phase species being controlled.

The apparatus (300) could include different design features. For example, the flow could split and go through several such apparatuses in parallel. As another example, several such apparatuses could be arranged in series in the flow. Also, different configurations for moving the denuding surfaces (320) could be used. For example, the apparatus could include several separate flexible sheets instead of a single sheet. Also, the denuding surfaces (320) could move in some other manner, such as in an oscillating motion where parts of the denuding surfaces could move into and out of the flow path and the treatment zone as they oscillate back and forth.

III. Techniques for Continuous Diffusion Denuding with Moving Denuding Surface

Referring now to FIG. 4, a technique for continuous diffusion denuding with a moving denuding surface will be discussed. The technique can include passing (410) a denuding gas flow along a denuding surface to concentrate one or more gas phase species from the denuding gas flow onto the denuding surface with a diffusion denuding action. The technique can also include moving (420) the denuding surface while continuing to concentrate the one or more gas phase species from the denuding gas flow onto the denuding surface. This moving could include a series of movements, as with a stepping motor that drives the denuding surface while gas is being concentrated on the denuding surface, or continuous movement, as with a continuously moving drive motor that drives the denuding surface. In either case, the denuding surface is moved without ceasing the denuding action, as would happen if the denuding surface were being entirely removed, leaving no denuding surface in place for some time, as in some batch denuding processes.

The one or more gas phase species could include a species selected from a group consisting of mercury, hydrochloric acid, and combinations thereof. The denuding surface can include a continuous surface, and the technique can include refreshing one or more denuding properties of the solid denuding surface while concentrating the one or more gas phase species from the gas flow onto the denuding surface.

The technique may further include sensing (430) and quantifying (440) quantities of at least one of the one or more gas-phase species. For example, the sensing (430) and quantifying (440) may be done with one or more of the types of sensors and data processing and reporting systems discussed above. The quantifying (440) may quantify the gas-phase species such as in terms of density on the denuding surface. The technique may further include receiving (450) data resulting from the sensing (430) and quantifying (440), processing (460), and reporting (470) results of the processing. For example, the processing (460) may include converting density values to concentration values, storing the density and/or concentration values, and representing the values in tables, graphs, etc. Reporting (470) may include displaying and/or transmitting representations of the data, such as in the form of such tables, graphs, etc. However, sensing (430), quantifying (440), receiving (450), processing (460), and/or reporting (470) may be omitted, such as if the technique is for emission control and not for analysis of species in emissions.

The denuding surface may be a surface of a flexible sheet, or some other surface such as the surface of a string, etc. The denuding surface can be oriented vertically while concentrating the one or more gas phase species from the gas flow onto the denuding surface. The denuding gas flow can be a portion of a main gas flow, such as a gas flow that has been redirected from the main gas flow. The denuding gas flow can be a portion of a slip gas flow that is a portion of the main flow, with the slip gas flow having been redirected from the main gas flow and the denuding gas flow having been redirected from the slip gas flow.

The denuding surface may be a surface of a reactive coating on a substrate, such as coating on a tape.

While the invention has been particularly shown and described with reference to preferred embodiments thereof, it will be understood by those skilled in the art that various changes in form and details may be made therein without departing from the spirit and scope of the invention.

I claim:

1. A denuding apparatus comprising:

a duct configured to receive a denuding gas flow;

a solid denuding surface positioned at least partially within the duct and configured to concentrate a gas-phase species from the denuding gas flow on the denuding surface;

a drive system connected to the solid denuding surface, the drive system being configured to move the solid denuding surface relative to the duct while the solid denuding surface is concentrating the gas-phase species from the denuding gas flow on the denuding surface; and a sensor configured to sense quantities of the gas-phase species concentrated on the denuding surface while the drive system moves the solid denuding surface relative to the duct and while the solid denuding surface is concentrating the gas-phase species from the denuding gas flow on the denuding surface.

2. The apparatus of claim 1, wherein the denuding surface comprises a continuous surface and the apparatus further comprises a treatment zone through which the solid denuding surface is configured to pass to refresh one or more denuding properties of the solid denuding surface.

3. The apparatus of claim 1, wherein the sensor is further configured to quantify quantities of the gas-phase species.

4. The apparatus of claim 3, further comprising a data processing and reporting system that is configured to receive data from the sensor, process the data, and reports results of the processing.

5. The apparatus of claim 1, wherein the denuding surface is a surface of a flexible sheet.

6. The apparatus of claim 1, wherein the denuding surface is oriented vertically while sampling the gas phase species.

7. The apparatus of claim 1, wherein the apparatus further comprises a slip stream flow duct leading from a main gas flow, the slip stream flow duct carrying a slip stream flow from which the denuding gas flow is received.

8. The apparatus of claim 1, wherein the denuding surface is a surface of a reactive coating on a substrate.

9. A denuding apparatus comprising:
a duct configured to receive a denuding gas flow;
a solid denuding surface positioned at least partially within the duct and configured to concentrate a gas-phase species from the denuding gas flow on the denuding surface;
a drive system connected to the solid denuding surface, the drive system being configured to move the solid denuding surface relative to the duct while the solid denuding surface is concentrating the gas-phase species from the denuding gas flow on the denuding surface; and
a sensor configured to sense quantities of the gas-phase species concentrated on a first portion of the denuding surface located outside the duct while the drive system moves the solid denuding surface relative to the duct and while the solid denuding surface is concentrating the gas-phase species from the denuding gas flow on a second portion of the denuding surface that is positioned within the duct.

10. The apparatus of claim 9, wherein the denuding surface comprises a continuous surface and the apparatus further comprises a treatment zone through which the solid denuding surface is configured to pass to refresh one or more denuding properties of the solid denuding surface.

11. The apparatus of claim 9, wherein the sensor is further configured to quantify quantities of the gas-phase species.

12. The apparatus of claim 11, further comprising a data processing and reporting system that is configured to receive data from the sensor, process the data, and report results of the processing.

13. The apparatus of claim 9, wherein the denuding surface is a surface of a flexible sheet.

14. The apparatus of claim 9, wherein the denuding surface is oriented vertically while sampling the gas phase species.

15. The apparatus of claim 9, wherein the apparatus further comprises a slip stream flow duct leading from a main gas flow, the slip stream flow duct carrying a slip stream flow from which the denuding gas flow is received.

16. The apparatus of claim 9, wherein the denuding surface is a surface of a reactive coating on a substrate.

17. A denuding apparatus comprising:
a duct configured to receive a denuding gas flow;
a solid denuding surface positioned at least partially within the duct and configured to concentrate a gas-phase species from the denuding gas flow on the denuding surface, the solid denuding surface being a surface of a reactive coating on a flexible sheet;
a drive system connected to the solid denuding surface, the drive system being configured to move the solid denuding surface relative to the duct while the solid denuding surface is concentrating the gas-phase species from the denuding gas flow on the denuding surface; and
a sensor configured to sense quantities of the gas-phase species concentrated on a first portion of the denuding surface located outside the duct while the drive system moves the solid denuding surface relative to the duct and while the solid denuding surface is concentrating the gas-phase species from the denuding gas flow on a second portion of the denuding surface that is positioned within the duct.

18. The apparatus of claim 17, wherein the sheet is a tape.

19. The apparatus of claim 17, wherein the sensor is further configured to quantify quantities of the gas-phase species.

20. The apparatus of claim 19, further comprising a data processing and reporting system that is configured to receive data from the sensor, process the data, and report results of the processing.

* * * * *